United States Patent
Jang et al.

(10) Patent No.: US 11,359,192 B1
(45) Date of Patent: Jun. 14, 2022

(54) METHOD FOR PREPARING DNA LIBRARY DERIVED FROM FFPE TISSUE USING ENDONUCLEASE

(71) Applicant: GenoPeaks Co., Ltd., Seoul (KR)

(72) Inventors: Se-Jin Jang, Seongnam-si (KR); Sung-Min Chun, Seoul (KR); Chang Ohk Sung, Yongin-si (KR); Yu Jin Kim, Seoul (KR); Ji-Young Lee, Seoul (KR); Hye-Joon Jeon, Seoul (KR)

(73) Assignee: GenoPeaks Co., Ltd., Seoul (KR)

( * ) Notice: Subject to any disclaimer, the term of this patent is extended or adjusted under 35 U.S.C. 154(b) by 307 days.

(21) Appl. No.: 16/347,199

(22) PCT Filed: Nov. 3, 2017

(86) PCT No.: PCT/KR2017/012421
§ 371 (c)(1),
(2) Date: May 3, 2019

(87) PCT Pub. No.: WO2018/084640
PCT Pub. Date: May 11, 2018

(30) Foreign Application Priority Data

Nov. 4, 2016 (KR) .................. 10-2016-0146642
Nov. 2, 2017 (KR) .................. 10-2017-0145331

(51) Int. Cl.
*C12N 15/10* (2006.01)
*C12Q 1/6806* (2018.01)
*C12N 9/50* (2006.01)

(52) U.S. Cl.
CPC ..... *C12N 15/1003* (2013.01); *C12N 15/1093* (2013.01); *C12Q 1/6806* (2013.01)

(58) Field of Classification Search
CPC ............ C12N 15/1003; C12N 15/1093; C12Q 1/6806
See application file for complete search history.

(56) References Cited

U.S. PATENT DOCUMENTS

2011/0104693 A1 5/2011 Seligmann
2013/0316913 A1 11/2013 Makarov et al.
(Continued)

FOREIGN PATENT DOCUMENTS

JP 2013-509863 A 3/2013

OTHER PUBLICATIONS

Laskowski et al. (Methods in Enzymology, 1980, 65:263-276) (Year: 1980).*

(Continued)

*Primary Examiner* — Jeremy C Flinders
(74) *Attorney, Agent, or Firm* — Revolution IP, PLLC

(57) ABSTRACT

The present invention relates to a method of preparing a DNA library derived from FFPE tissue using endonucleases, and the majority of general clinical samples are FFPE tissues and in case of old FFPE tissues, DNA library preparation often fails and NGS analysis becomes difficult and therefore there is a desperate need to overcome these problems. S1 nucleases are enzymes which specifically cleave only single-stranded DNA and in almost all FFPEs, there is a nick in the dsDNA everywhere, which can be the target of S1 nucleases. In the process of extracting gDNA from FFPE tissues, since when S1 nucleases are treated and eluted under appropriate conditions during elution, a DNA fragment can be obtained with DNA having a size suitable for DNA library preparation together with the DNA extraction, the Covaris fragmentation process can be omitted and cost and time can be reduced.

12 Claims, 12 Drawing Sheets

(56) References Cited

U.S. PATENT DOCUMENTS

2015/0031556 A1    1/2015  Barrett et al.
2016/0265027 A1*   9/2016  Sanches-Kuiper ..........................
                                                    C12N 15/1093

OTHER PUBLICATIONS

International Search Report for PCT/KR2017/012421 dated Feb. 21, 2018 from Korean Intellectual Property Office.
Parkinson, Nicholas J. et al., "Preparation of high-quality next-generation sequencing libraries from picogram quantities of target DNA", Genome Research, 2012, vol. 22, No. 1, pp. 125-133.
Hedegaard, Jakob et al., "Next-Generation Sequencing of RNA and DNA Isolated from Paired Fresh-Frozen and Formalin-Fixed Paraffin-Embedded Samples of Human Cancer and Normal Tissue", PloS One, 2014, vol. 9, No. 5, e98187, inner pp. 1-16.

* cited by examiner

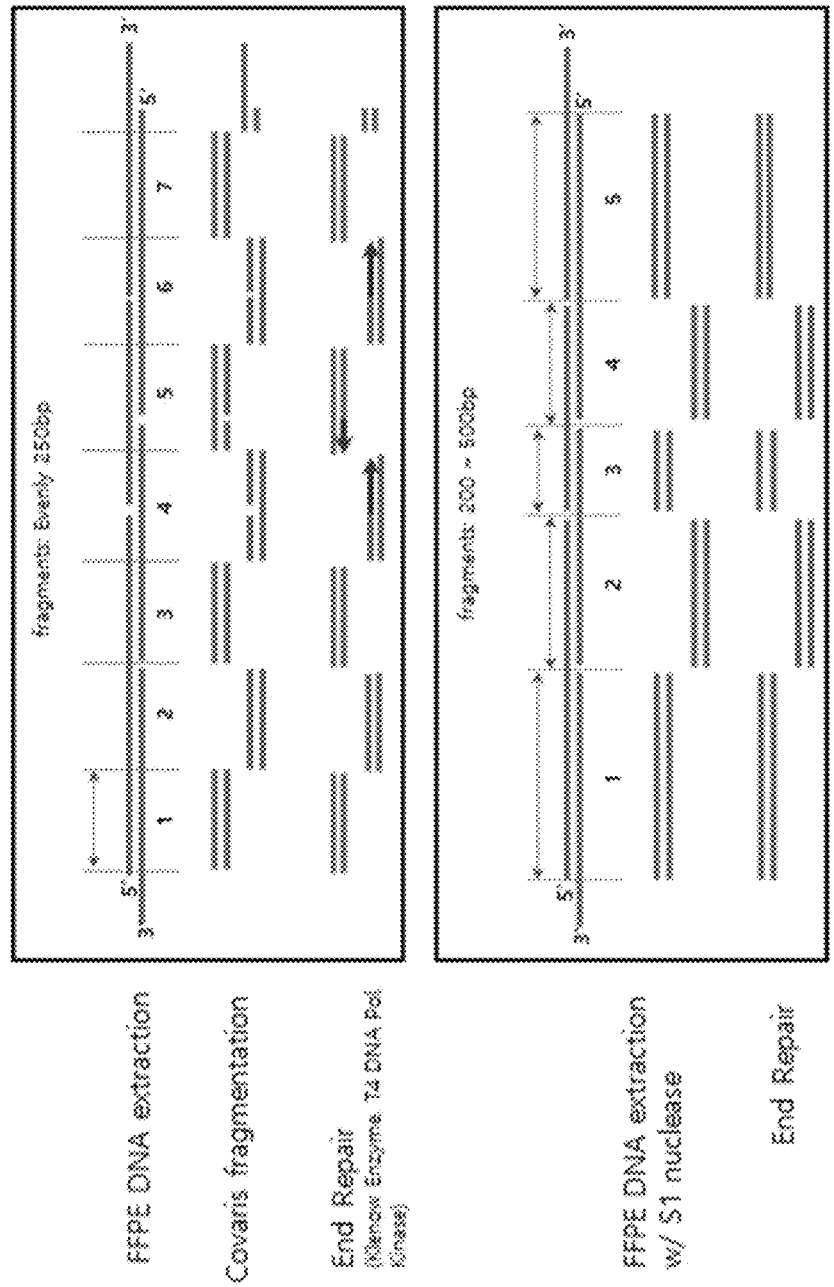
[FIG. 1]

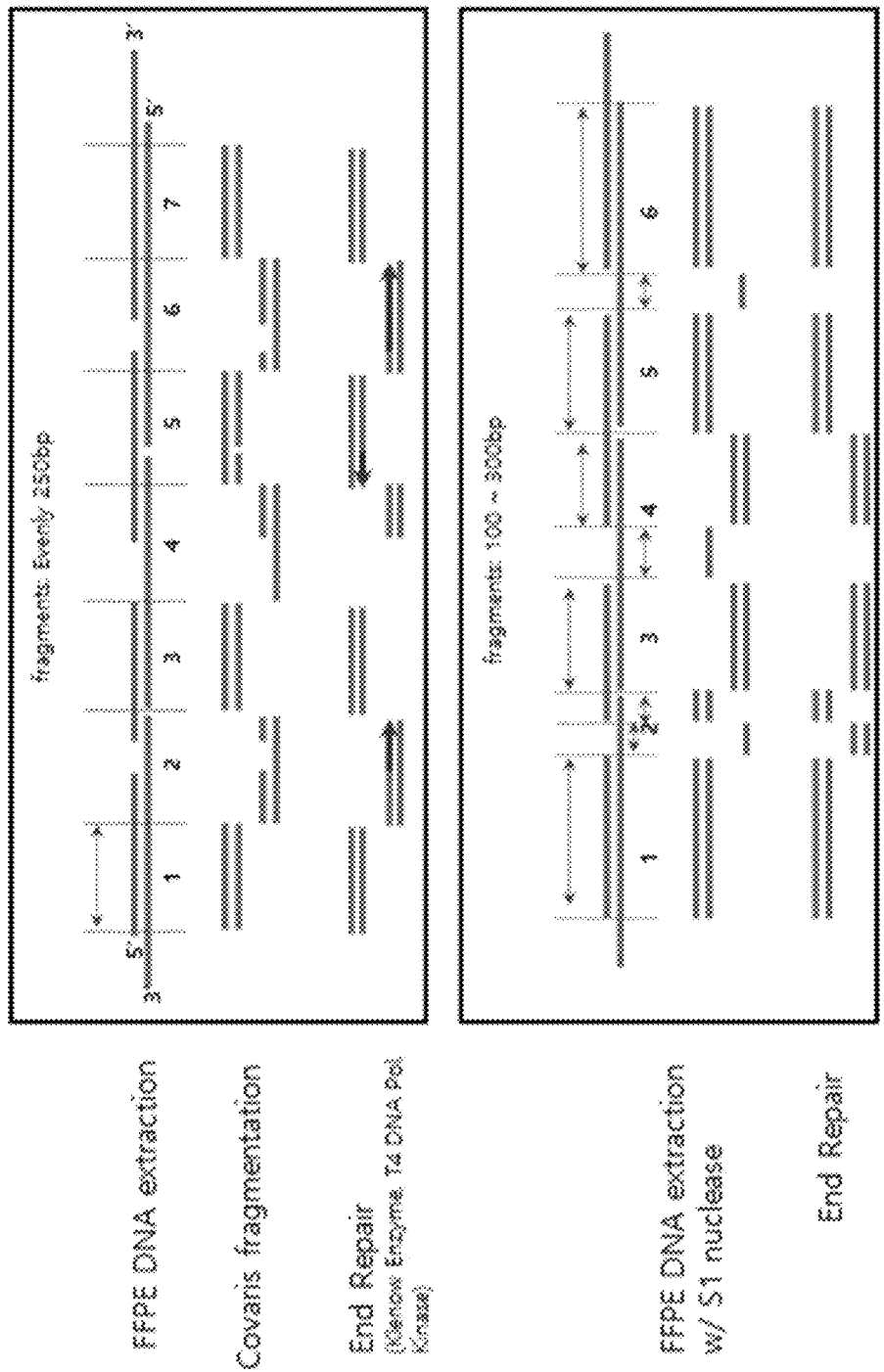
[FIG. 2]

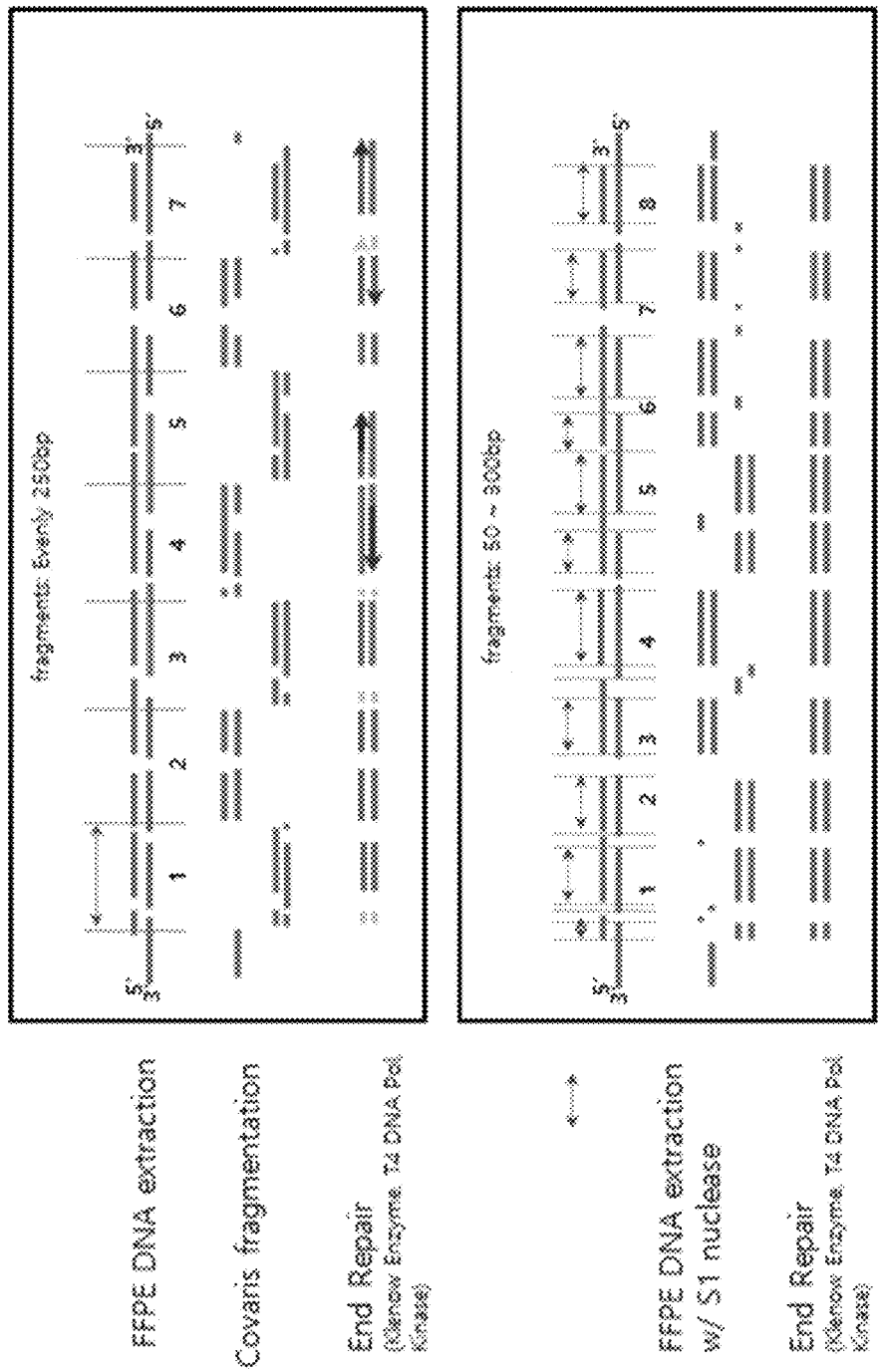
[FIG. 3]

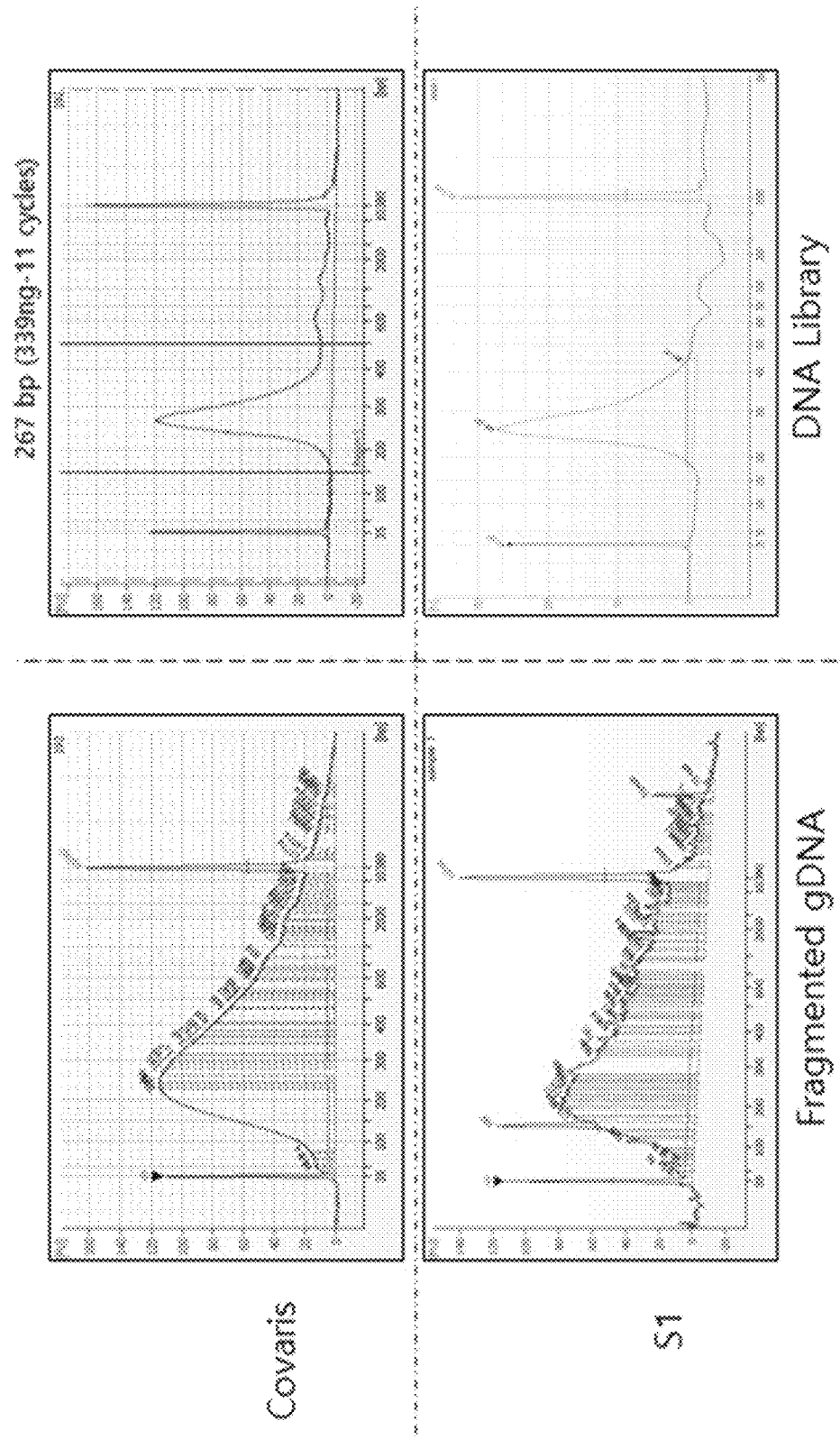
[FIG. 4]

[FIG. 5]
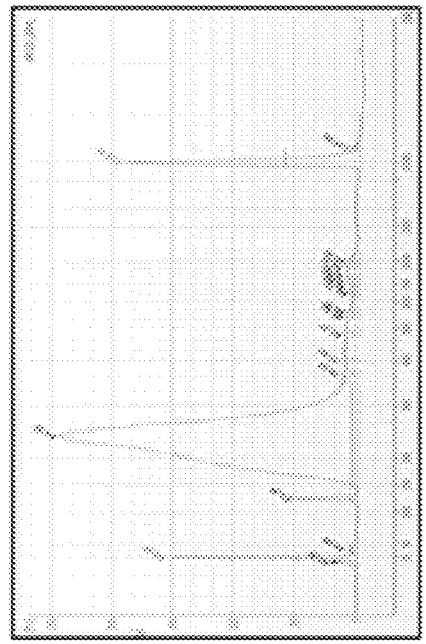
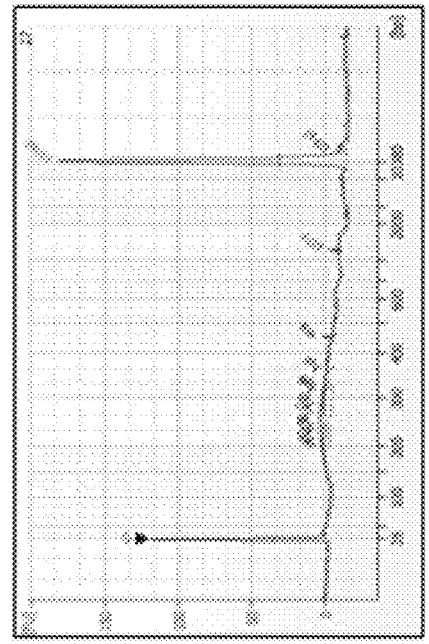
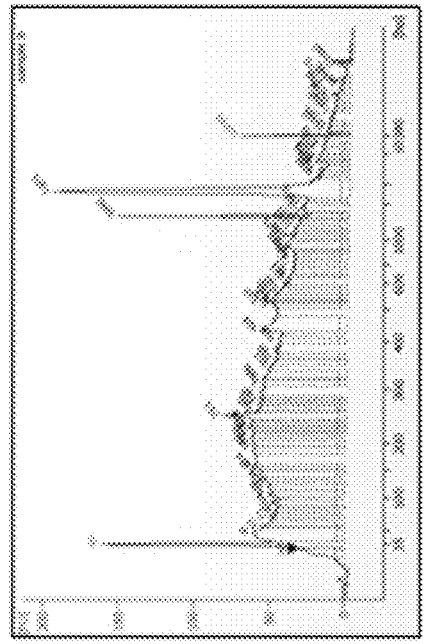
02S-50906_B4 (#27) — QC2 Fail (15.7ng) — Covaris — S1 — Fragmented gDNA — DNA Library

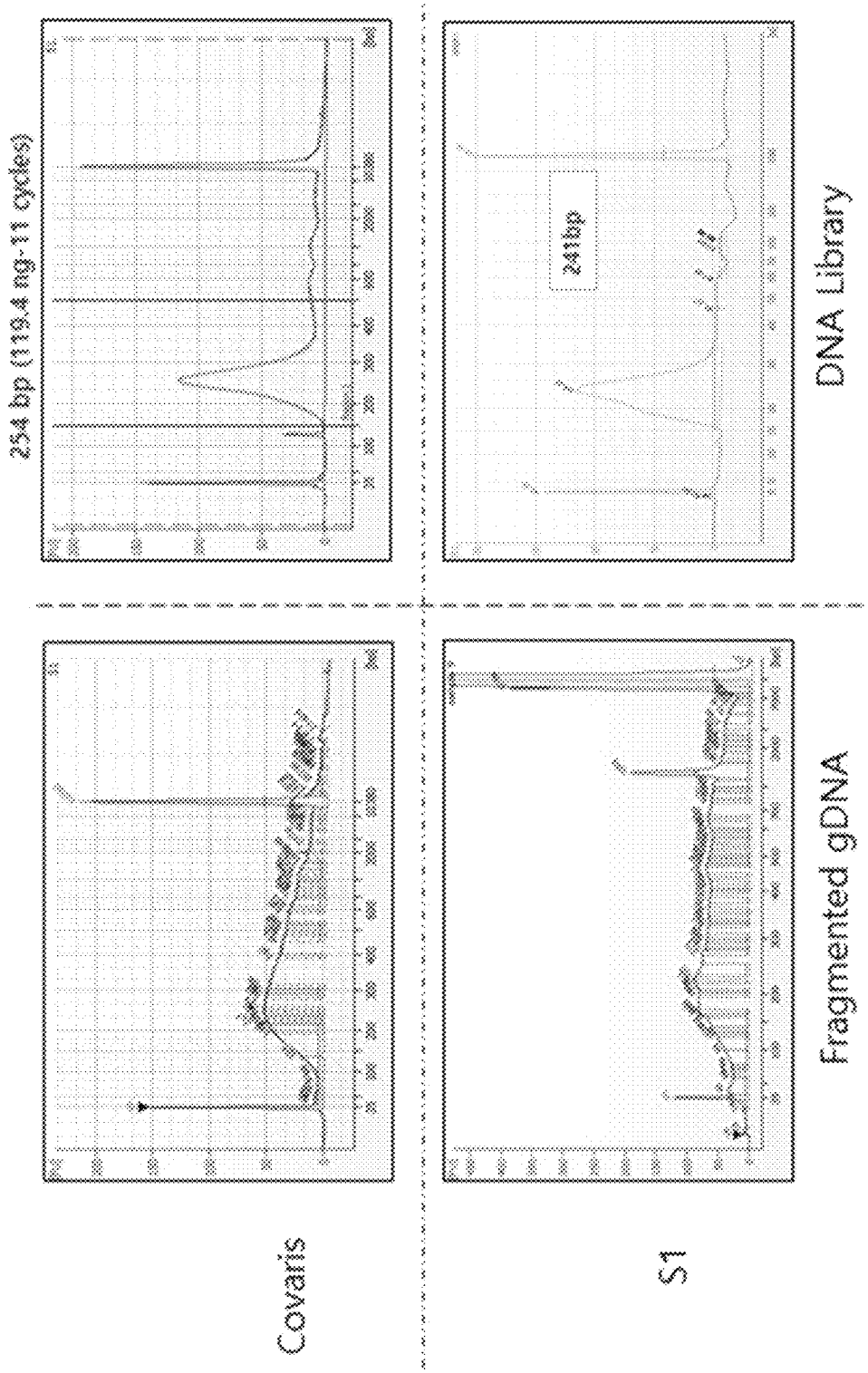
[FIG. 6]

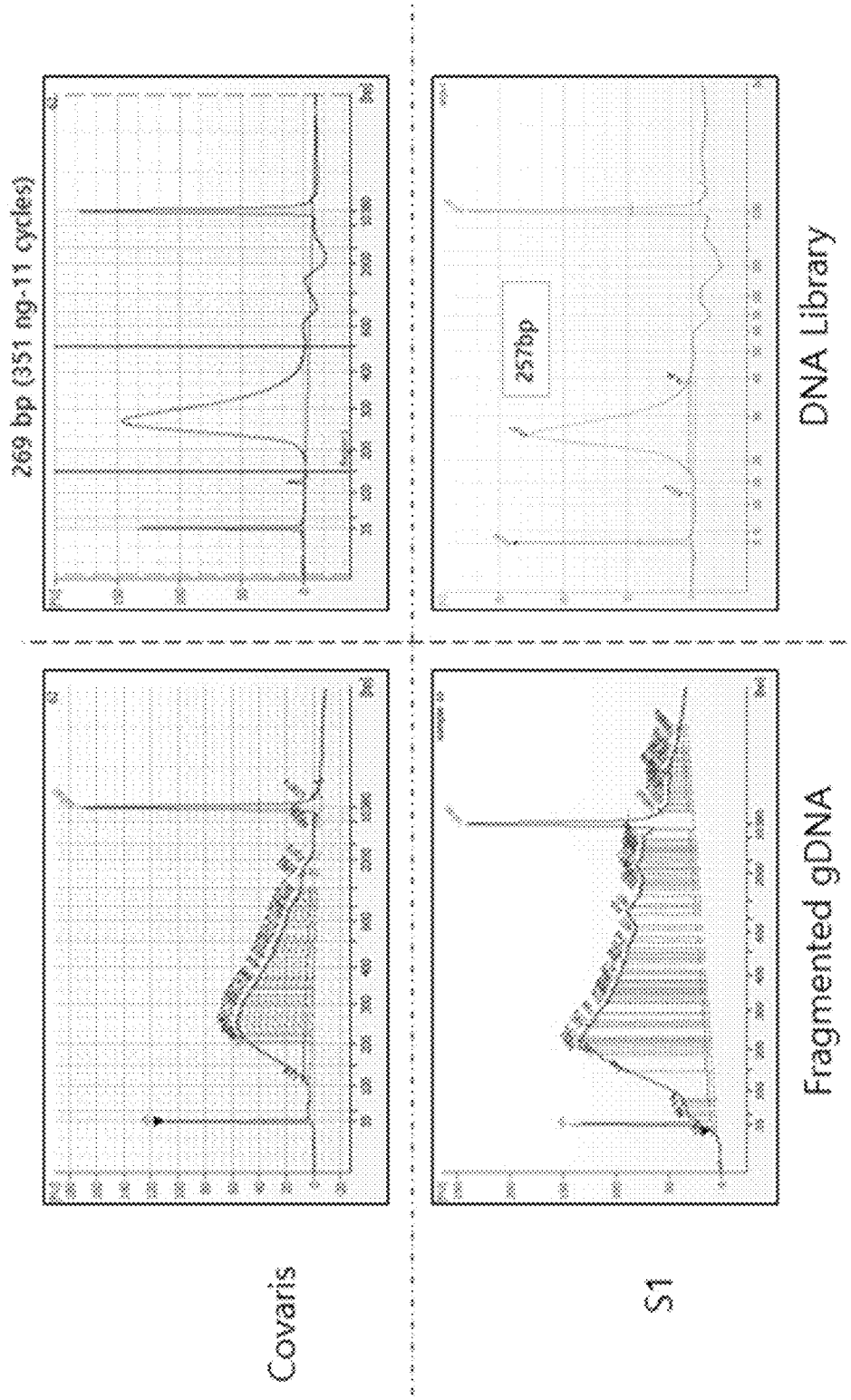
[FIG. 7]

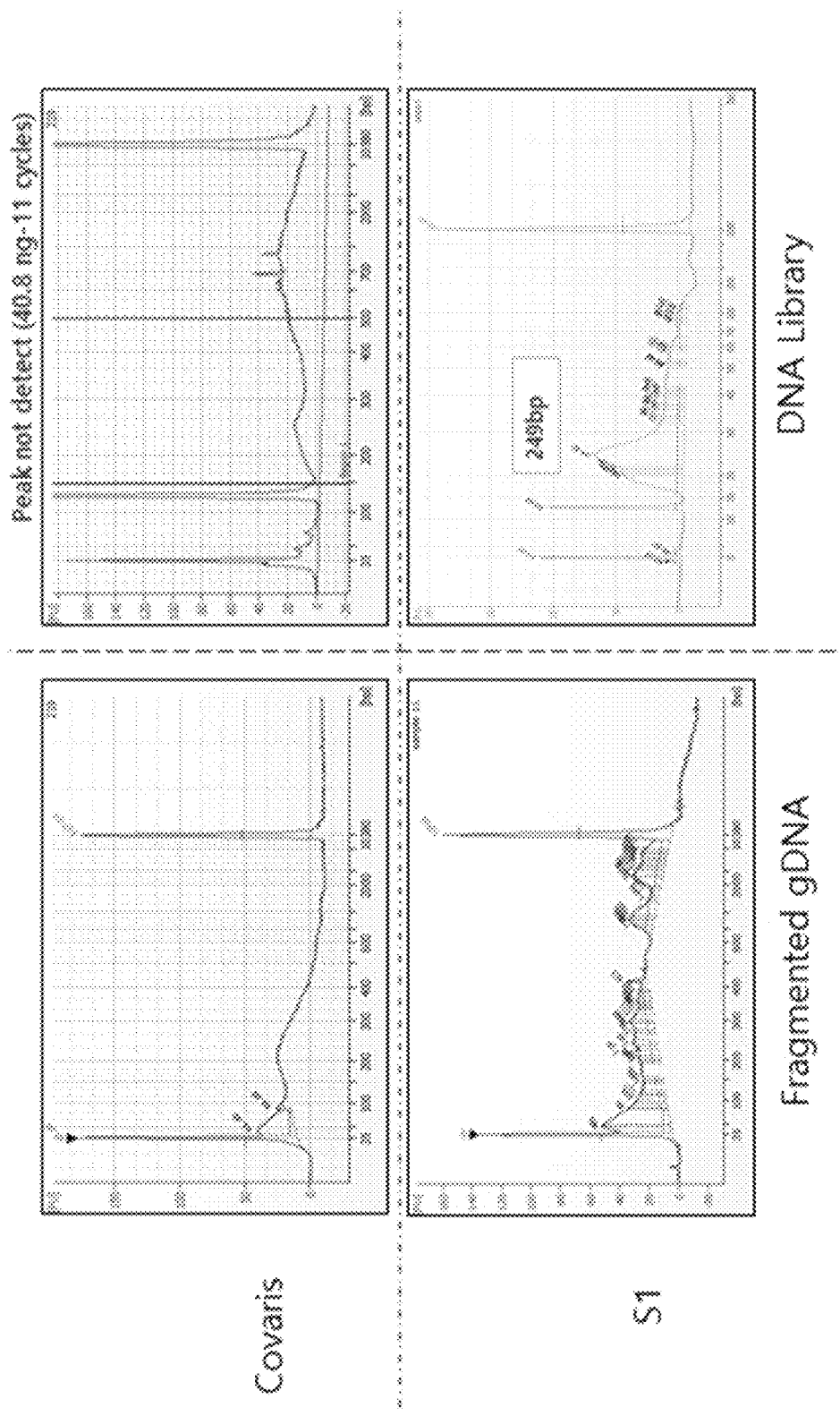
[FIG. 8]

[FIG. 9]
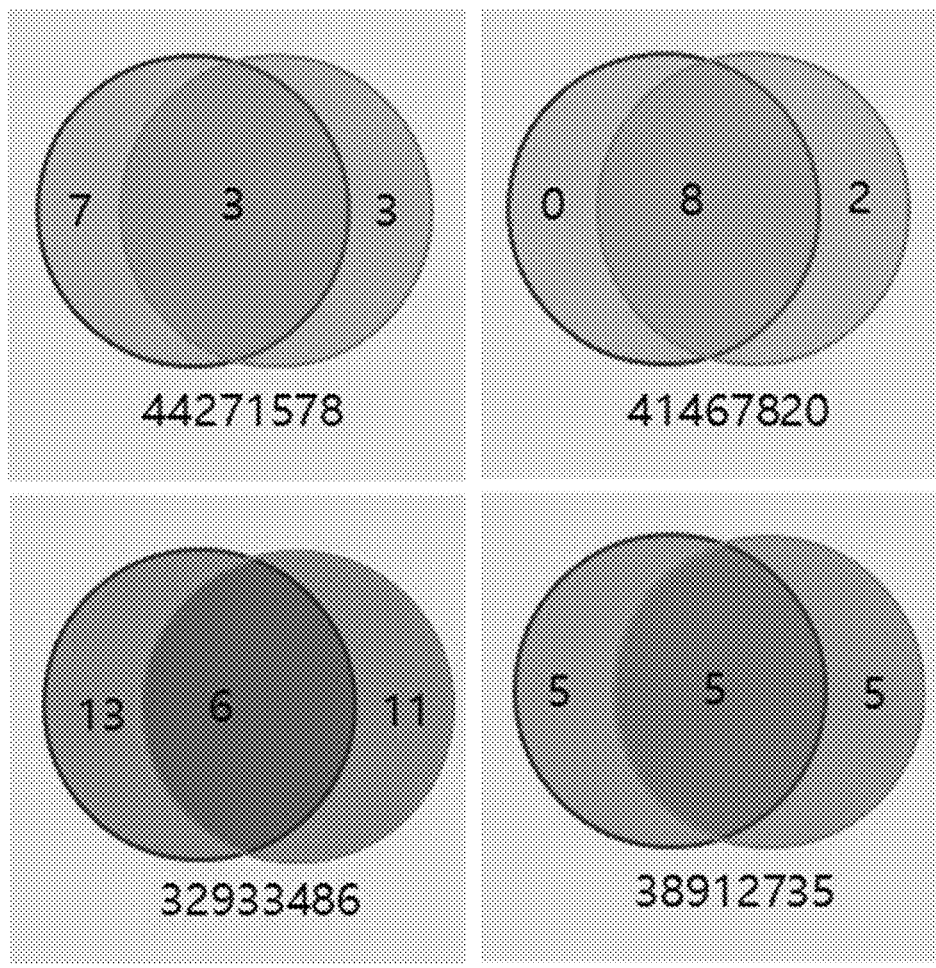

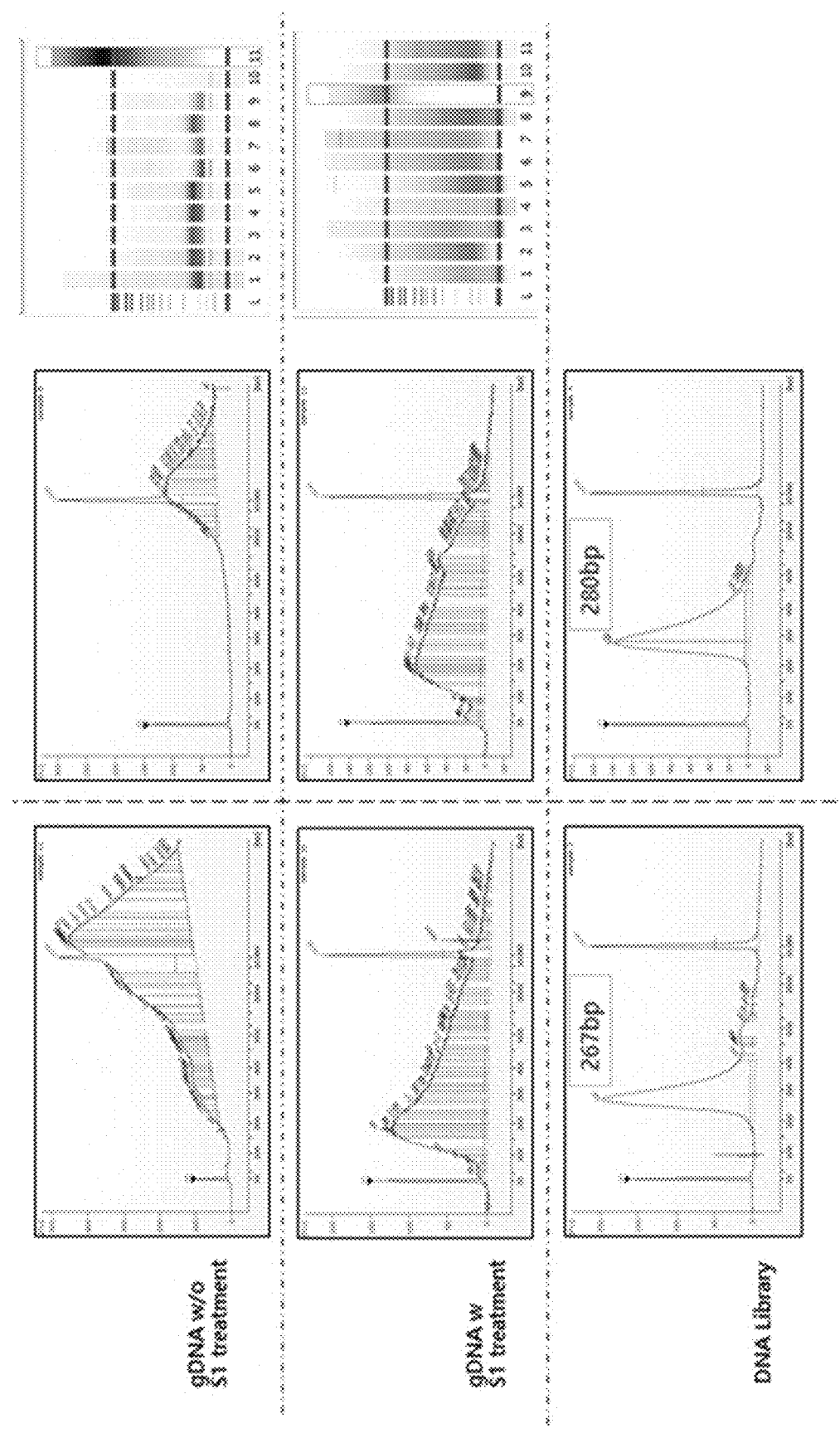
[FIG. 10]

[FIG. 11]
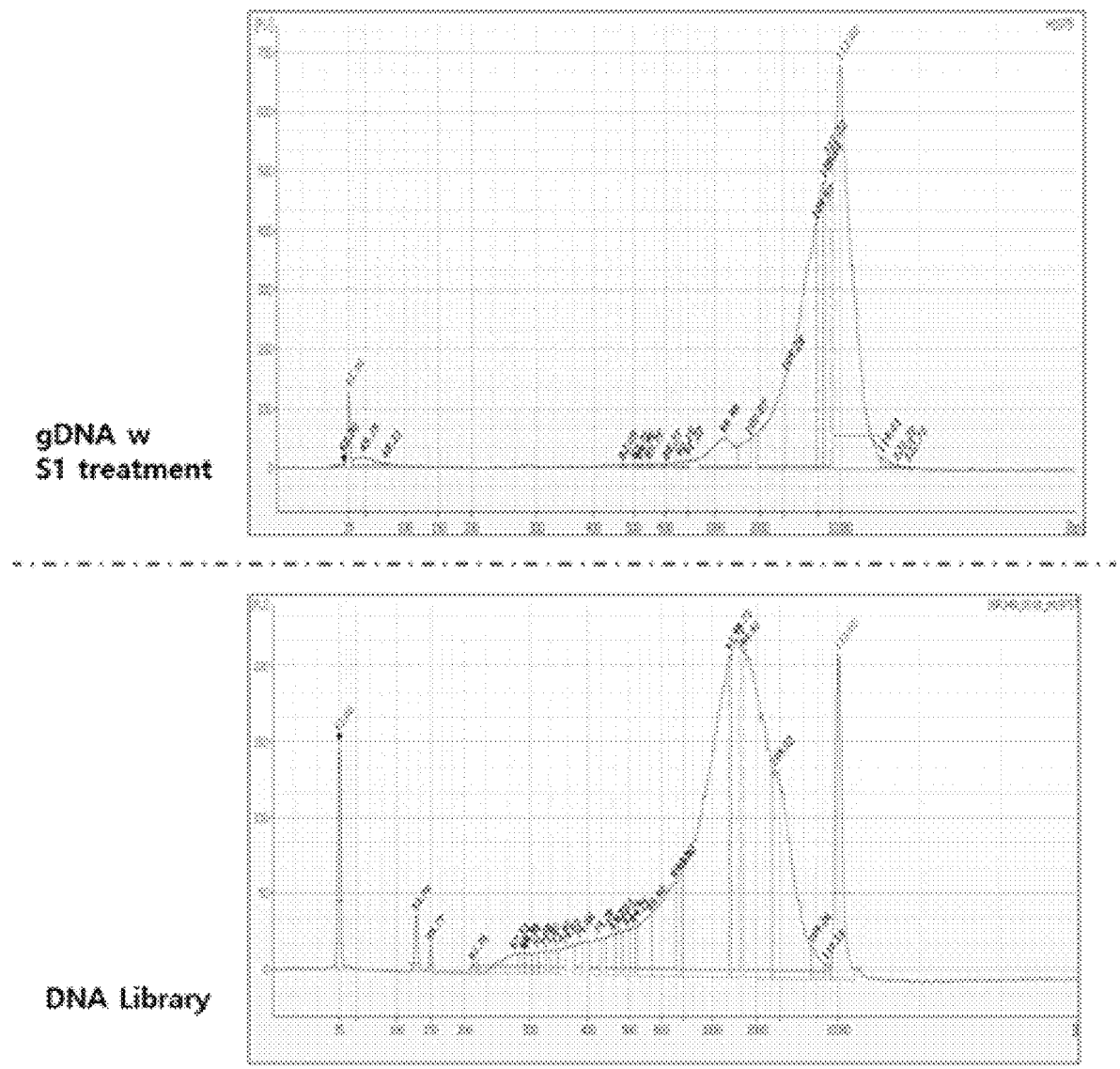

[FIG. 12]
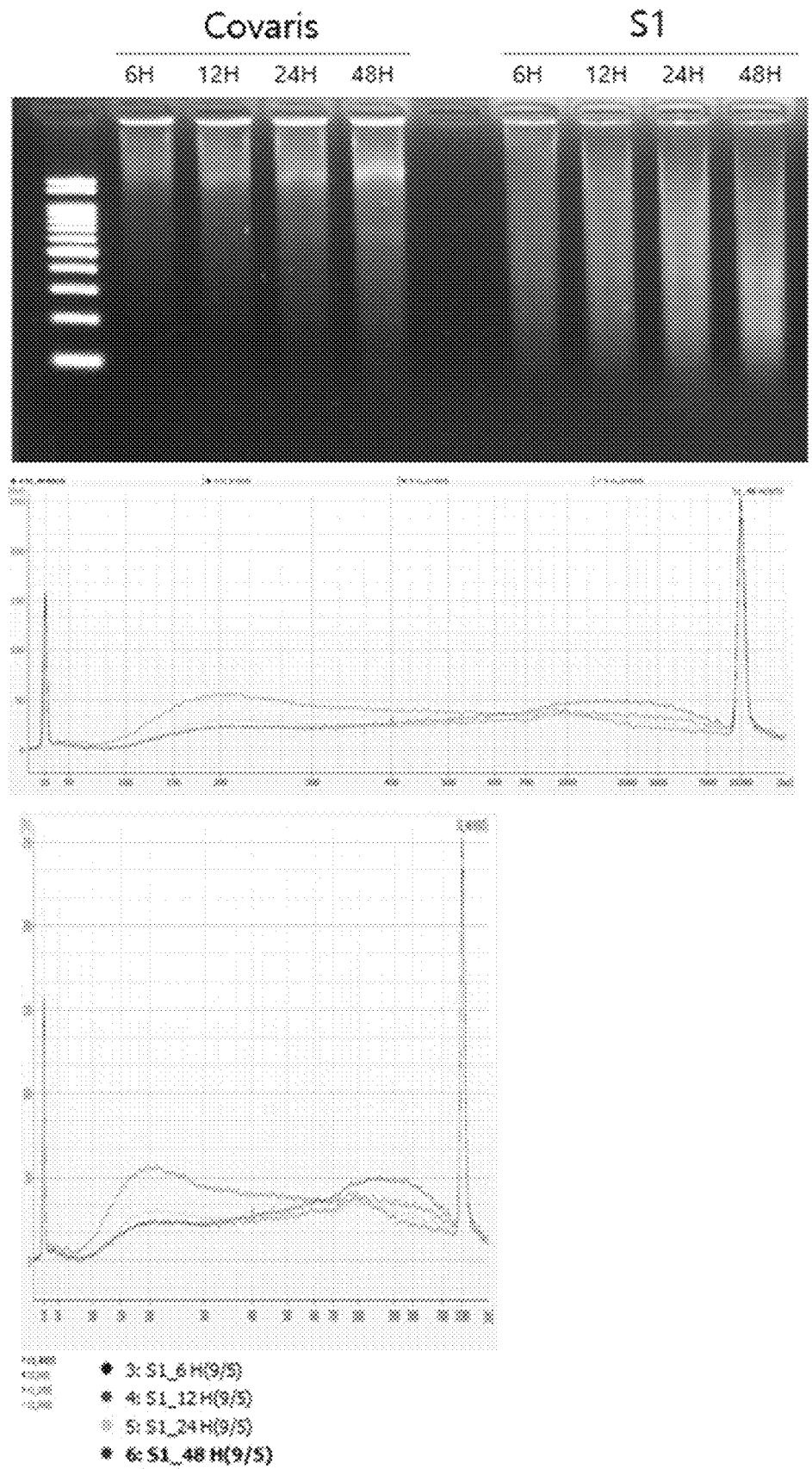

METHOD FOR PREPARING DNA LIBRARY DERIVED FROM FFPE TISSUE USING ENDONUCLEASE

TECHNICAL FIELD

The present invention relates to a method of preparing a DNA library derived from formalin-fixed, paraffin-embedded (FFPE) tissue using an endonuclease.

BACKGROUND ART

Recently, molecular biology techniques have been widely used in the medical field. In particular, in terms of molecular pathology, these techniques can diagnose pathologically from the morphological level to the genetic level, and also reveal the genetic characteristics of the specific disease from the morphological level and gene level. For this diagnostic procedure, the hospital collects the tissue in the form of FFPE, and from the FFPE tissue, genetic information related to various clinical conditions can be analyzed and diagnosed.

For next generation sequencing (NGS) analysis, a DNA library should be prepared by extracting genomic DNA (gDNA) from a sample, fragmenting the extracted genomic DNA in a size of about 150 to 250 bp, selecting and extracting DNA of the corresponding size, and subjecting to end-repair using various enzymes. When using gDNA of normal quality, a DNA library can be prepared through the above process, however, in case of old and much degraded DNA, DNA library preparation often fails. In the case of DNA fragmentation, a sonication method e.g. using Covaris apparatus is generally used. It controls the size of the final fragmented DNA by adjusting the output and reaction time and at this time, since the location of fragmentation on DNA occurs randomly, already severely degraded gDNA extracted from old samples is fragmented into finer pieces, thereby resulting in failure of DNA library preparation.

Endonuclease is a generic term for enzymes that produce oligoribonucleotides by cleaving 3',5'-phosphodiester bonds inside the polynucleotide chain, without distinguishing between DNA and RNA. S1 nuclease, a kind of endonucleases, is an enzyme that binds only one strand of double-stranded DNA and targets the region, and it produces two pieces of fragmented DNA having double helix structure or removes by cutting the DNA of single strand structure. In molecular biology, S1 nucleases are commonly used to remove single-stranded ends from DNA molecules or to remove open hairpin loops during the synthesis of double-stranded cDNA, in order to create a blunt end.

The majority of common clinical samples are FFPE tissues and in the case of old FFPE tissues, NGS analysis is difficult because of the above problems and therefore, there is an urgent need to overcome this problem. Therefore, the present inventors confirmed that almost all the FFPEs have a nick in the dsDNA all over, and this part can be a target of S1 nucleases, and the preparation efficiency of the NGS library can be greatly increased by using the S1 nucleases.

DISCLOSURE

Technical Problem

It is an object of the present invention to provide a composition for preparing a DNA library of FFPE tissue-derived DNA comprising an endonuclease as an active ingredient, and a method of preparing a DNA library of FFPE tissue-derived DNA by using the same.

Also, another object of the present invention is to provide a composition for eluting FFPE tissue-derived DNA comprising an endonuclease as an active ingredient, and a method of eluting FFPE tissue-derived DNA by using the same.

Technical Solution

In order to achieve the above object, the present invention provides a composition for preparing a DNA library of FFPE tissue-derived DNA comprising endonuclease as an active ingredient.

Also, the present invention provides a kit for preparing a DNA library of FFPE tissue-derived DNA comprising the composition.

In addition, the present invention provides a composition for eluting FFPE tissue-derived DNA comprising endonuclease as an active ingredient.

Furthermore, the present invention provides a kit for eluting FFPE tissue-derived DNA comprising the composition.

In addition, the present invention provides a method of preparing a DNA library having improved complexity comprising: in a method of preparing a DNA library derived from FFPE tissue, reacting by treating the FFPE tissue slice lysate with an endonuclease; and eluting the DNA from a reaction product.

Further, the present invention provides a method of eluting FFPE tissue-derived DNA comprising: reacting by treating the FFPE tissue slice lysate with an endonuclease; and eluting the DNA from a reaction product.

The present invention also provides uses of endonuclease for the preparation of DNA library of FFPE tissue-derived DNA.

Also, the present invention provides the use of endonuclease for eluting FFPE tissue-derived DNA.

Advantageous Effects

The present invention relates to a method of preparing a DNA library derived from FFPE tissue using endonucleases. The majority of general clinical samples are FFPE tissues and in case of old FFPE tissues, DNA library preparation often fails and NGS analysis becomes difficult and therefore there is a desperate need to overcome these problems. S1 nucleases are enzymes which specifically cleave only single-stranded DNA and in almost all FFPEs, there is a nick in the dsDNA everywhere, which can be the target of S1 nucleases. In the process of extracting gDNA from FFPE tissues, since when S1 nucleases are treated and eluted under appropriate conditions during elution, a DNA fragment can be obtained with DNA having a size suitable for DNA library preparation together with the DNA extraction, the Covaris fragmentation process can be omitted and cost and time can be reduced. In addition, it is possible to perform end-repair without additional fragmentation, so it can be inhibited from not being used as ligation insert owing too small a piece and can increase the complexity of the prepared library.

DESCRIPTION OF DRAWINGS

FIG. 1 shows a Covaris method generally used for DNA fragmentation and a DNA fragmentation process using S1 nucleases of the present invention using DNA in good condition.

FIG. 2 shows a Covaris method generally used for DNA fragmentation and a DNA fragmentation process using S1 nucleases of the present invention using DNA in intermediate condition.

FIG. 3 a Covaris method generally used for DNA fragmentation and a DNA fragmentation process using S1 nucleases of the present invention using DNA in bad condition.

FIG. 4 shows DNA size changes and DNA library preparation results after S1 nuclease treatment using patient FFPE tissue (#192).

FIG. 5 shows DNA size changes and DNA library preparation results after S1 nuclease treatment using patient FFPE tissue (#27).

FIG. 6 shows DNA size changes and DNA library preparation results after S1 nuclease treatment using patient FFPE tissue (#51).

FIG. 7 shows DNA size changes and DNA library preparation results after S1 nuclease treatment using patient FFPE tissue (#62).

FIG. 8 shows DNA size changes and DNA library preparation results after S1 nuclease treatment using patient FFPE tissue (#219).

FIG. 9 shows the comparison of mutation detection results obtained using the library prepared by the Covaris method and the library prepared by the S1 nuclease treatment method.

FIG. 10 shows the result of preparing a library using FFPE tissue in a good condition.

FIG. 11 shows the result of preparing a library by extracting DNA from the unfixed fresh cells by the S1 nuclease treatment method.

FIG. 12 shows the results obtained by extracting gDNA from A549 cell block fixed with formaldehyde for various times (6, 12, 24, 48 hours) by Covaris method and S1 nuclease treatment method followed by confirming the pattern of DNA extracted from Bioanalyzer and 1.5% agarose gel.

BEST MODE

The present invention provides a composition for preparing a DNA library of FFPE tissue-derived DNA comprising endonuclease as an active ingredient. Specifically, the endonuclease may cleave a nick which is single-stranded DNA derived from FFPE tissue as a target.

Preferably, the DNA library is for next generation sequencing (NGS) analysis, but it is not limited thereto.

The term "formalin-fixed, paraffin-embedded (FFPE)" in the present invention is a method for keeping or storing tissue isolated from an animal and it means that the tissue is fixed and the fixed tissue is embedded in the wax. The specific process for preparing the FFPE tissue, though it is not limited thereto, may be as follows:

First, tissue is removed from animal specimens by incision or biopsy. The tissue is then cut to prepare slices and fixed in order to be prevented from corruption or degradation and to be inspected clearly under microscope for histologic, pathological or cytological studies. Fixation is the process of immobilizing, killing and preserving tissue for the purpose of staining and viewing under a microscope. Post-processing allows the tissue to penetrate the dyeing reagent and crosslink the macromolecules, stabilizing and trapping them on the spot. Many fixative solutions such as Bouine solution, formalin or liquid nitrogen are used for this purpose. The fixed tissue is then embedded in wax, cut into thin sections and allowed to stain by hematoxylin and eosin staining. Subsequently, microtoming is performed by microscopic sectioning so as to study the staining with antibody under a microscope.

On the other hand, as for FFPE tissues to be used for fragmentation of FFPE tissue-derived DNA of the present invention, not only recently produced but also FFPE tissues that have been stored for at least 10 years can be applied.

The term "endonuclease" in the present invention refers to a generic term for enzymes that produce oligoribonucleotides by cleaving 3',5'-phosphodiester bonds inside the polynucleotide chain, without distinguishing between DNA and RNA.

On the other hand, in the present invention, all endonuclease can be applied. Preferably, S1 nuclease, P1 nuclease, mung bean nuclease or BAL-31 nuclease can be applied, but it is not limited thereto.

The term "S1 nuclease" in the present invention is an enzyme which specifically cleaves only single-stranded DNA and in almost all FFPEs, there is a nick in the dsDNA everywhere, which can be the target of S1 nucleases.

In addition, the present invention provides a kit for preparing a DNA library of FFPE tissue-derived DNA comprising the composition.

On the other hand, the kit may include other instruments, solutions and the like that are generally used for preparing a DNA library of FFPE tissue-derived DNA, but it is not limited thereto.

Also, the present invention provides a composition for eluting FFPE tissue-derived DNA comprising endonuclease as an active ingredient.

In addition, the present invention provides a kit for eluting FFPE tissue-derived DNA comprising the composition.

On the other hand, the kit may additionally include other instruments, solutions and the like which are generally used for eluting FFPE tissue-derived DNA, but it is not limited thereto.

Further, the present invention provides a method of preparing a DNA library having improved complexity comprising: in a method of preparing a DNA library derived from FFPE tissue, reacting by treating the FFPE tissue slice lysate with an endonuclease; and eluting the DNA from a reaction product.

In detail, the FFPE tissue slice lysate may be obtained by decomposing a protein from the FFPE tissue slice and removing it and the step of eluting DNA from the reaction product may further comprise subjecting to end-repair of both ends of the DNA and ligating the end-repaired DNA.

Preferably, the step of reacting by treating the FFPE tissue slice lysate with an endonuclease may comprise treating the endonuclease with 1 to 100 units and may comprise treating the endonuclease at 37° C. for 1 to 60 minutes, but it is not limited thereto.

Preferably, the DNA library is for NGS analysis, but it is not limited thereto.

Further, the present invention provides a method of eluting FFPE tissue-derived DNA comprising: reacting by treating the FFPE tissue slice lysate with an endonuclease; and eluting the DNA from a reaction product.

Particularly, the FFPE tissue slice lysate may be obtained by decomposing a protein from the FFPE tissue slice and removing it.

Preferably, the step of reacting by treating the FFPE tissue slice lysate with an endonuclease may comprise treating the endonuclease with 1 to 100 units and may comprise treating the endonuclease at 37° C. for 1 to 60 minutes, but it is not limited thereto.

On the other hand, in a method for preparing a DNA library or a method of eluting DNA of the present invention, all endonucleases can be applied, and preferably, S1 nuclease, P1 nuclease, mung bean nuclease or BAL-31 nuclease can be applied, but it is not limited thereto.

The present invention also provides uses of endonuclease for the preparation of DNA library of FFPE tissue-derived DNA.

Also, the present invention provides the use of endonuclease for eluting FFPE tissue-derived DNA.

Hereinafter, the present invention will be described in detail with reference to the following examples. It should be noted, however, that the following examples are illustrative of the present invention and are not intended to limit the scope of the present invention. The examples of the present invention are provided to more fully describe the present invention to those skilled in the art.

<Example 1> Comparison of Fragmentation Using FFPE-Derived DNA in Various Conditions A Covaris method generally used for DNA fragmentation and a DNA fragmentation process using S1 nucleases of the present invention were compared using DNAs in good, intermediate and bad conditions (FIG. 1 to FIG. 3).

The Covaris method consists of the following steps: After extracting gDNA from a sample and fragmenting the extracted gDNA to a size of about 150 to 250 bp, DNA of the corresponding size is selected and subjected to end repair using various enzymes. Then, A-tailing at the 3' end and ligation using adapter sequences are performed.

When using gDNA of normal quality, a DNA library can be prepared through the above process, however, in case of old and much degraded DNA, DNA library preparation often fails. Already severely degraded gDNA extracted from old samples is fragmented into finer pieces, thereby resulting in failure of DNA library preparation.

Particularly, in the case of FFPE tissues which have been a long time since it was made, DNA fragmentation is already proceeding much, and when random fragmentation using Covaris is repeated again, a region that is cleaved into small pieces forms. This part is removed during the process of size selection after preparing the library (only the library size is 150 bp or more selected), resulting in the loss of the entire gDNA information, thereby decreasing the complexity of the prepared library.

In contrast, in the case of gDNA extracted using the S1 nucleases of the present invention, much more sites are conserved and the complexity of the library is increased.

<Example 2> Confirmation of DNA Size Change after S1 Nuclease Treatment

In order to confirm how the size of DNA changes after S1 nuclease treatment actually, DNA was extracted by using FFPE tissue for 5 patients and the size of extracted DNA was measured by using BioAnalyzer.

When DNA was extracted by the usual method using Covaris, gDNA of a smearing pattern of 150 bp~10 kb was confirmed as expected.

On the other hand, it was confirmed that, as expected, the fragmentation of a specific size mainly occurred without wide distribution of DNA size when S1 nuclease was treated in the elution process (20 units, 10 min). In addition, it was confirmed that the size thereof ranges within 150 to 250 bp required for DNA library preparation. It was confirmed that appropriate DNA of 150-250 bp size can be extracted by treating S1 nuclease during extraction of gDNA from FFPE tissue.

Specifically, in the case of the #192 sample, the DNA library was well prepared by both methods, and a slightly larger DNA library was prepared in the Covaris method (FIG. 4).

In the case of the #27 sample, the amount of the DNA selected and extracted after fragmentation by the Covaris method was too small to proceed to the next step, and the DNA library was not prepared, however, the DNA library was successfully prepared by the S1 nuclease treatment method (FIG. 5).

In the case of the #51 and #62 samples, both methods succeeded in preparing DNA libraries (FIG. 6 and FIG. 7).

In the case of the #217 sample, there was a problem in the form of the DNA library prepared by the Covaris method, and it was impossible to use it in the NGS analysis, but the DNA library was successfully prepared by the S1 nuclease treatment method (FIG. 8)

<Example 3> Optimization of S1 Nuclease Treatment Conditions

The optimal condition was established by variously comparing the treatment conditions of S1 nucleases such as the used amount and the reaction time of S1 nucleases. The treatment conditions for S1 nucleases are shown in Table 1.

TABLE 1

| Condition | S1 Unit | Incubation @ 37° C. |
| --- | --- | --- |
| A | 20 units | 10 min |
| B | 20 units | 30 min |
| C | 10 units | 10 min |
| D | 10 units | 2 min |
| E | 2 units | 10 min |
| F | 2 units | 2 min |

As a result, it was confirmed that a library showing some differences according to the conditions was produced.

The library size tended to be smaller as the concentration of S1 nucleases was higher or the reaction time was longer.

The produced amount of library tended to increase as the concentration of S1 nucleases was higher or the reaction time was longer.

The active site of the S1 nucleases was present in the FFPE DNA and it is confirmed to be fragmented due to this.

The increased amount of library prepared means that the number of moles of insert, DNA fragmented and generated by S1, which can be ligated with the adapter, has increased, i.e. the complexity of the library is increased. Therefore, protocol B (20 unit, 30 min) was considered to be the optimum condition so as to increase the complexity of the library. However, this is optimal among the compared conditions, and protocol B is not limited to the final optimal condition, and more efficient optimal conditions can be changed through additional comparison analysis.

<Example 4> Capture Sequencing

Whether there was no problem in analyzing the mutation of the library prepared by S1 nuclease treatment method using targeted NGS or not was actually confirmed.
1. Capture panel: using Tier 2 panel (cancer panel targeting genes of 200 or more)
2. Library pooling
(1) Capture by pooling eight libraries barcoded at each different index.
(2) The eight libraries for 5 DNA used in the comparative experiments of libraries according to said each different S1 nuclease reaction conditions were as follows (Table 2).
 i) Five libraries prepared by protocol B
 ii) Three libraries prepared by protocol A
(3) Pooling 56~80 ng depending on the size of each library.

In the library prepared using protocol B, the depth was much higher than the protocol A library despite the smaller size, and the same results were obtained in all three patients compared.

As described in Example 3, the complexity of the library prepared by protocol B was high, which proved that the duplication rate was lower in the library of the protocol B method than in the library of the protocol A method.

In addition, because the size is smaller than protocol A and even though the same amount is used, the mole number will be higher, the number of total reads is proved to be higher in the library of the protocol B method than that in the library of the protocol A method.

On the other hand, even a small-sized library prepared by S1 nucleases was able to obtain values at problem-free level for sequence analysis.

TABLE 2

| No | # | Pathology number | Patient number | Protocol | S1 | Incu Time | OP_ID | Qubit Library Con. (ng/ul) | total, ng | From 150 to 500 (pg/ul) dilution (bio-analyzer) | From 150 to 500 (ng/ul) bio-analyzer | Average size (bp) | peak | Library for capturing (ng) |
|---|---|---|---|---|---|---|---|---|---|---|---|---|---|---|
| 1 | 192 | 10S_091623_A1 | 27335989 | A | 20 U | 10 min | 16R209_0001_27335989 | 9.0 | 270.6 | 1399.41 | 12.62 | 289 | 263 | 65 |
| 1 | 192 | 10S_091623_A1 | 27335989 | B | 20 U | 30 min | 16R214_0002_27335989 | 16.8 | 504.0 | 1889.22 | 31.74 | 281 | 256 | 56 |
| 2 | 27 | 02S_50906_B4 | 28042413 | A | 20 U | 30 min | 16R219_0004_28042413 | 4.6 | 138.6 | 2173.95 | 10.04 | 242 | 238 | 80 |
| 3 | 51 | 08S_62322_B3 | 32247565 | A | 20 U | 10 min | 16R211_0005_32247565 | 6.8 | 203.4 | 1008.07 | 6.83 | 240 | 241 | 80 |
| 3 | 51 | 08S_62322_3 | 32247565 | B | 20 U | 30 min | 16R224_0006_32247565 | 4.0 | 120.0 | 2402.42 | 9.61 | 248 | 242 | 80 |
| 4 | 62 | 09S_60473_2 | 27176699 | A | 20 U | 30 min | 16R229_0008_37176699 | 25.6 | 768.0 | 1770.5 | 45.32 | 277 | 257 | 56 |
| 5 | 219 | 08S_58509_A4 | 20611846 | A | 20 U | 10 min | 16R213_0025_20611846 | 3.9 | 117.0 | 857.21 | 3.34 | 276 | 249 | 80 |
| 5 | 219 | 08S_58509_A4 | 20611846 | B | 20 U | 30 min | 16R234_0009_20611846 | 6.4 | 192.0 | 1471.94 | 9.42 | 238 | 236 | 80 |

After sequencing the libraries with the above conditions, the results of the analysis between the libraries prepared by the protocol A and the protocol B were compared using the values of the QC metrics, and the library results of the small size were confirmed (Table 3).

TABLE 3

| Sample ID | lane | % Pool Representation | % Exprected Representation |
|---|---|---|---|
| 16R209_2733589T | 1 | 6.5 | 12.5 |
| 16R214_27335989T | 1 | 10.9 | 12.5 |
| 16R219_28042413T | 1 | 16.5 | 12.5 |
| 16R211_32247565T | 1 | 9.8 | 12.5 |
| 16R224_32247565T | 1 | 20.3 | 12.5 |
| 16R229_37176699T | 1 | 11.6 | 12.5 |
| 16R213_20611846T | 1 | 8.8 | 12.5 |
| 16R234_20611846T | 1 | 12.2 | 12.5 |
| NNNNNN | 1 | 3.1 | 0 |
| unused | 1 | 0.3 | 0 |

| Sample ID | Number of Total Reads | % PF Reads | % Selected Bases | Mean Target Coverage | % Target Not Covered | % Targets Bases Covered 30X | % Duplication |
|---|---|---|---|---|---|---|---|
| 16R209_0001_27335989T | 4146704 | 87.9 | 52 | 61.543011 | 1.2 | 82.6 | 44.3 |
| 16R214_0002_27335989T | 6950550 | 87.8 | 62.8 | 179.57019 | 1 | 96.1 | 21.2 |
| 16R219_0004_28042413T | 10536642 | 86.3 | 41.3 | 146.86531 | 0.9 | 97.4 | 40.7 |
| 16R211_0005_32247565T | 6259226 | 86.5 | 48.7 | 102.68804 | 0.9 | 96.3 | 39 |
| 16R224_0006_32247565T | 12911684 | 86.3 | 43 | 178.54504 | 0.9 | 98.3 | 41.9 |
| 16R229_0008_37176699T | 7386386 | 87.1 | 62 | 215.59911 | 0.9 | 97.5 | 17.8 |
| 16R213_0025_20611846T | 5573858 | 85.9 | 46.5 | 57.878794 | 0.9 | 90 | 53.7 |
| 16R234_0009_20611846T | 7794250 | 85.7 | 47.3 | 129.84997 | 1 | 95.9 | 33.6 |

In the smallest libraries of 236 bp (16R234_0009_20611846) and 238 bp (16R219_0004_28042413), the following QC metrics values could be obtained.

Duplication rate: 33.6%, 40.7%
On target rate (% of selected bases): 47.3%, 41.3%
>30× rate: 95.9%, 97.4%
Mean target coverage: 129.8×, 146.8×

Of course, it was lower value than the larger library (library prepared from DNA in better-condition: 16R214_0002_2733598, 16R229_0008_37176699).

Duplication rate: 21.2%, 17.8%
On target rate (% of selected bases): 62.8%, 62%
>30× rate: 97.4%, 97.5%
Mean target coverage: 179.5×, 215.6×

However, considering that the covaris method failed to prepare a library and could not perform the sequence analysis itself, and the level at which there is no significant problem in genetic variation analysis is at least mean coverage 100×, it was confirmed that the small size library prepared by the S1 nuclease treatment method can be sufficiently utilized for NGS analysis.

<Example 5> Comparison of Somatic Variants

Its value can be analyzed on the above QC metrics, but it is confirmed if the genetic variation can be detected with the actual corresponding analysis result.

The agreement degree of somatic variants with five samples used in the experiment was compared.

The OncoMap_V4 panel is a method to amplify a short PCR product of about 100 bp and to confirm a specific hot spot mutation using the MassArray system. The mutation that can be confirmed by the OncoMap_V4 panel is identified as 41 genes of 473 hot spot mutations. Among 5 samples, hot spot mutations of the EGFR and MLH1 genes were detected in 3 samples and were not detected in 2 samples (Table 4).

As a result, it was confirmed that the genetic mutation exactly coincided with the mutation result confirmed by OncoMap_v4 in 5 samples.

TABLE 4

| S1 protocol | OP_ID | Library size (bp) | Patient_ID | Sample ID | Surgical_no_sub | Patients # |
|---|---|---|---|---|---|---|
| A | 16R209_27335989T | 263 | 27335989 | 192 | 10S-091623_A1 | 65 |
| B | 16R214_27335989T | 256 | 27335989 | 192 | 10S-091623_A1 | 65 |
| B | 16R219_28042413T | 238 | 28042413 | 27 | 02S-50906_B4 | 24 |
| A | 16R211_32247565T | 241 | 32247565 | 51 | 08S-62322_B3 | 49 |
| B | 16R244_32247565T | 242 | 32247565 | 51 | 08S-62322_B3 | 49 |
| B | 16R229_37176699T | 257 | 33373955 | 62 | 09S-60473_2 | 59 |
| A | 16R213_20611846T | 249 | 26011846 | 219 | 08S-58509_A4 | 88 |
| B | 16R234_20611846T | 236 | 20611846 | 219 | 08S-58509_A4 | 88 |

| S1 protocol | Primary (1), recur (2) | Organs | OncoMap_V4_Result | Mr. Juhan Kim_LAB Result (PGM) | S1_treated_DNA_tier2 Analysis Result |
|---|---|---|---|---|---|
| A | 2 | lung | EGFR_L858R, EGFR_T790M, | not_tested | EGFR, L858R (10%), EGFR_T7890M (21%) |
| B | 2 | lung | EGFR_L858R, EGFR_T790M, | not_tested | EGFR, L858R (13%), EGFR_T7890M (15%) |
| B | 2 | Primary | EGFR_L747_P753>S | too_low_depth (average_depth, 4) | EGFR_L747_P753 delinsS (45%) |
| A | 1 | lung | Nd | too_low_depth (average_depth, 9) | Nd |
| B | 2 | lung | Nd | too_low_depth (average_depth, 9) | Nd |
| B | 2 | brain | Nd | not_tested | Nd |
| A | 1 | Primary | MLH1_V384D, EGFR_L858R, | not_tested | MLH1_V384D (34%), EGFR_L858R (48%) |
| B | 1 | Primary | MLH1_V384D, EGFR_L858R, | not_tested | MLH1_V384D (52%), EGFR_L858R (22%) |

<Example 6> Comparison of Library Quality (Covaris Vs S1 Nucleases Treatment)

Using the same sample of the FFPE tissue of the patient sample that already had the results, the library prepared by the Covaris method and the library prepared by the S1 nuclease treatment method (protocol B method) were pooled, captured simultaneously and NGS analyzed and the value of the results were compared directly. For four samples, each library was prepared, pooled, and captured using a Tier 2 panel, followed by sequencing using the MiSeq v3 kit.

From the value of the result by comparing QC Metrics, it was confirmed that the results obtained from the S1 nuclease treatment method were superior to the Covaris fragmentation method (Table 5).

Number of total reads: Capture uses the same amount of library, but the S1 nuclease treatment method shows much higher sequencing reads in most samples.

Mean target coverage: The S1 nuclease treatment method shows much higher values in all samples.

% target >30×: The S1 nuclease treatment method shows much higher values in all samples.

% duplication: The S1 nuclease treatment method shows much lower values in all samples. This means that the complexity of the prepared DNA library is higher.

TABLE 5

| | | | Library | | | | | |
|---|---|---|---|---|---|---|---|---|
| | | | | | | | Loading | |
| Patient # | Surgical # | OP_ID | Prep method | Amount (ng) | Peak size (bp) | Capture Amount (ng) | Con. (pM) | Cluster density |
| 44271578 | 12S 92016_A5 | 15R102_001_44271578T | Covaris | 450.0 | 274 | 50 | 15 | 1355 |
| 41467820 | 11S 50993_D1 | 15R144_005_41467820T | | 399.0 | 284 | 50 | | |
| 32933486 | 06S 39202_1 | 15R128_008_32933486T | | 128.4 | 248 | 70 | | |
| 38912735 | 09S 689904 | 15R131_0010_38912735T | | 169.2 | 253 | 70 | | |
| 44271578 | 12S 92016_A5 | 16R345_0013_44271578 | S1, protocol B | 546.0 | 259 | 50 | | |
| 41467820 | 11S 50993_D1 | 16R346_0014_41467820T | | 600.0 | 261 | 50 | | |
| 32933486 | 06S 39202_1 | 16R347_0015_32933486T | | 267.0 | 250 | 70 | | |
| 38912735 | 09S 68904 | 16R348_0016_38912735T | | 159.0 | 241 | 70 | | |

| | | | | QC Metrics | | | | |
|---|---|---|---|---|---|---|---|---|
| Patient # | Number of Total Reads | % PF Reads | % Selected Bases | Mean Target Coverage | % Target Bases Not Covered | % Targets Bases Covered 30X | % Duplication | |
| 44271578 | 5496564 | 89.7 | 49.2 | 115 | 0.9 | 92.9 | 11 | |
| 41467820 | 4665242 | 90.3 | 51.6 | 95 | 0.9 | 88.3 | 11.7 | |
| 32933486 | 7361098 | 89.2 | 41.8 | 113 | 0.8 | 93 | 25.3 | |
| 38912735 | 9559316 | 89.3 | 38.8 | 148 | 0.7 | 97.1 | 25.2 | |
| 44271578 | 7051726 | 89.7 | 46.6 | 150 | 0.6 | 95 | 8.9 | |
| 41467820 | 804426 | 89 | 46.4 | 177 | 0.9 | 96.4 | 10.1 | |
| 32933486 | 9346052 | 88.7 | 42.7 | 181 | 0.5 | 95.9 | 15.3 | |
| 38912735 | 9472126 | 86.8 | 38.3 | 172 | 0.8 | 97.5 | 17.3 | |

In addition, it was confirmed if mutation results obtained using the library prepared by respective method were consistent (FIG. 9 and Table 6).

For mutations detected simultaneously in both methods, both depth (total depth and variant allele depth) were all at least 30×.

The variant allele fraction was high enough as 30% or higher. Higher depths were established in the mutants obtained from the libraries prepared by the S1 nuclease treatment method. This implies an increase in the reliability of the result value.

In the case of the mutations detected in only each method, as for depth, S1 was higher in total depth and was similar at 2-4× level in variant allele depth. The variant allele fraction was similar at 6-13% level. In the case of the mutect algorithm used for single nucleotide variation analysis using NGS data, it has high possibility to be a false positive if the variant allele depth is less than 5×.

TABLE 6

| | Average values of all variants identified in both libraries | | | | | |
|---|---|---|---|---|---|---|
| | Total depth | | Variant allele depth | | Variant allele % | |
| Sample | Covaris | S1 | Covaris | S1 | Covaris | S1 |
| 44271578 | 82 | 87 | 30 | 30 | 36 | 33 |
| 41467820 | 92 | 129 | 55 | 71 | 56 | 52 |

TABLE 6-continued

| | Average values of all variants identified in both libraries | | | | | |
|---|---|---|---|---|---|---|
| | Total depth | | Variant allele depth | | Variant allele % | |
| Sample | Covaris | S1 | Covaris | S1 | Covaris | S1 |
| 32933486 | 93 | 147 | 37 | 60 | 40 | 43 |
| 38912735 | 84 | 80 | 41 | 39 | 48 | 48 |

TABLE 6-continued

| | Average values of all variants identified in both libraries | | | | | |
|---|---|---|---|---|---|---|
| | Total depth | | Variant allele depth | | Variant allele % | |
| Sample | Covaris | S1 | Covaris | S1 | Covaris | S1 |
| 44271578 | 49 | 39 | 3 | 2 | 6 | 6 |
| 41467820 | 0 | 26 | 0 | 2 | 0 | 9 |
| 32933486 | 35 | 61 | 2 | 4 | 6 | 7 |
| 38912735 | 22 | 39 | 2 | 3 | 13 | 7 |

Based on the variant allele depth 5×, it is confirmed if how many variants were detected in the covaris method and the S1 nuclease treatment method, respectively. If the number of variant allele is at least depth 5×, it was determined to be true positive and two variants were further detected in the S1 nuclease treatment method. If the number of variant allele is less than depth 5×, it was determine to be false positive and three variants were further detected in the Covaris method (Table 7).

In other words, in case of using the library prepared by the S1 nuclease treatment method, it is considered that a higher reliability can be obtained.

TABLE 7

| | Number of variant allele based on depth 5X | | | |
|---|---|---|---|---|
| | At least 5X | | Less than 5X | |
| Sample | Covaris | S1 | Covaris | S1 |
| 44271578 | 3 | 3 | 4 | 3 |
| 41467820 | 2 | 8 | 0 | 2 |
| 32933486 | 6 | 8 | 13 | 9 |
| 38912735 | 5 | 5 | 5 | 5 |

<Example 7> Preparation of Library Using FFPE Tissue in Bad Condition

The library was constructed by S1 nuclease method using 89 samples which failed to prepare library by Covaris method and as a result, 66.3% of the samples were successfully prepared library of which the level is suitable for NGS sequencing (Table 8).

TABLE 8

| | Good | Moderate | Bad | Fail |
|---|---|---|---|---|
| standard | Amount: 80 ng or more Size: 230 bp or more Only a single peak appears in library | Amount: 50 ng or more Size: 190 bp or more Two peaks appears in library | Size: less than 200 bp Amount: 80 ng or more Two peaks and adapter dimer appears in library | Proper peak is not appeared or amount is less then 20 ng |
| Count number | 25 | 34 | 19 | 11 |
| | Library prep success (66.3%) | | Library prep failure (33.7%) | |

<Example 8> Preparation of Library Using FFPE Tissue in Good Condition

Fresh FFPE tissue was also subjected to S1 nuclease treatment to confirm whether fragmented DNA for NGS could be obtained. In the case of old FFPE tissue, there is nick which is a target that the S1 nucleases can act to cause fragmentation, but in the case of fresh FFPE tissue recently made with FFPE, it is not known whether such nick exists and therefore for confirmation, DNA libraries were prepared using two FFPEs prepared three days before and using the conventional gDNA extraction method without S1 nuclease and the gDNA extraction method using S1 nuclease, respectively (Table 9).

Sizes of extracted gDNA and DNA libraries were identified using BioAnalyzer. As expected, gDNA extracted by the conventional method had a size of 10 kb or more. In contrast, it was confirmed that the gDNA extracted by the S1 nuclease treatment method was cleaved to about 200 bp (FIG. 10).

The library was constructed using the corresponding gDNA and the size of the library was confirmed, and as a result, it was confirmed that a library of a suitable size of 270-280 bp was produced in sufficient quantity. DNA extraction for constructing NGS library was successful by the S1 nuclease treatment method even though fresh FFPE tissue which has been 3 days since its production is used. In other words, this means that DNA fragmented in appropriate size for preparing a library for NGS can be extracted by S1 nuclease treatment method in all FFPE tissues.

Since it was confirmed that there is also nick which is an active site of the S1 nuclease in the fresh FFPE tissue, it was found that the nick was formed during fixation with formaldehyde. To confirm this, DNA was extracted from fresh, unfixed cells by the S1 nuclease treatment method and a library was prepared using the extracted DNA (FIG. 11). As expected, the gDNA size appears near 10 kb, which means that DNA fragmentation by S1 nucleases has not occurred. When the library was constructed using the gDNA, it was confirmed that a large library of at least 1.5 kb was produced.

This is a completely different result from the gDNA extracted by the S1 nuclease treatment method in fresh FFPE. Namely, there is nicks, which are active sites in which S1 nuclease can function in fresh FFPE DNA but three is not in cell line DNA. It was confirmed that nicks were also present at intervals of about average 200 bp on the fresh FFPE which has been 3 days since its production.

TABLE 9

| | | | Nanodrop | | | Qubit | |
|---|---|---|---|---|---|---|---|
| No | Pathology number | Condition | Con. (ng/ul) | 260/ 280 | 260/ 230 | Con. (ng/ul) | ND/ QB |
| 1 | 16S 68577 A5 | 1.5X | 110.1 | 1.91 | 1.82 | 13.6 | 8.10 |
| 2 | 16S 68784 A1 | | 387.3 | 1.97 | 2.07 | 54.8 | 7.07 |
| 3 | 16S 68577 A5 | SI Prep | 103 | 1.85 | 1.65 | 15.8 | 6.52 |
| 4 | 16S 68784 A1 | (1.5X Prep(S1 Nuclease 20 U/ul) + 37° C., 30 min + lysis buffer 100 ul + 1.5X prep (PEG 225 ul) | 218.4 | 1.91 | 1.82 | 39 | 5.60 |

In conclusion, S1 nuclease treatment during DNA extraction in FFPE tissues could obtain gDNA fragments of appropriate size without any fragmentation essentially required for NGS library preparation. This can skip the first step in preparing an NGS library, thereby having a significant reduction effect in time and cost. When the library was prepared using the fragmented DNA thus obtained, the success rate of library preparation was much higher than that of the conventional covaris method for fragmentation.

In addition, compared with the covaris method, a much higher depth could be obtained when using the library prepared by the S1 nuclease treatment method. It is also possible to prepare a library for NGS with a very high success rate even in very old FFPE tissues and to prepare library in the same way in very fresh FFPE tissues, and it proved that the S1 method can be a standard for NGS fragments of all FFPE tissues.

<Example 9> Confirmation of if Nicks Generated on DNA of FFPE Tissues are Targets of S1 Nucleases The nicks present on the DNA of the FFPE tissues occur during the formaldehyde fixation process for the preparation of FFPE tissue and the S1 nucleases react with the nick as the target.

When SNV was at least 3× and indel was at least 5×, they was used as a reliable variant.

26 variants were identified in all 8 libraries.

Each one BRAF_V600E variant was identified in each of the four libraries prepared by the Covaris method and the S1 nuclease treatment method, but the allele fraction was low and the mapping quality was also low to less than 30 as a result of IGV.

Three variants were identified only in the Covaris sample and 4 variants were identified only in the S1 nuclease-treated sample, all of which were proved to be false positives with a depth of 2 or 3.

On the other hand, as a result of the QC metrics comparison, the library prepared by Covaris method using DNA with long formaldehyde fixation time had lower peak size and total amount of libraries, lowered mean depth and increased duplication rate. In the case of the S1 method, the tendency of the amount of the library to be lowered is the same, but it was produced in amount of much more than the Covaris method. The peak size of the library was unchanged. Rather, the mean depth was increased which is caused by a small number of nicks that are the active site of S1 in the case of DNA with a short fixation time, and the duplication rate also increases. However, its degree is very lower than that of covaris.

TABLE 10

| Cell line | OP_ID | Prep method | Library A-mount (ng) | Peak size (bp) | Capture A-mount (ng) | Loading Con. (pM) | Cluster density | Number of Total Reads | % PF Reads | Target Selected Bases | Mean Coverage | % Target Not Covered | % Targets Bases Covered 30X | % Duplication |
|---|---|---|---|---|---|---|---|---|---|---|---|---|---|---|
| A549 | 16R546_0003_A549006T | Covaris | 585.0 | 280 | 70 | 12 | 1468 | 8157594 | 85 | 48.9 | 136.7 | 1 | 96.1 | 12.3 |
| A549 | 16R547_0004_A549012T | | 552.0 | 280 | 70 | | | 8212636 | 86.7 | 49.2 | 134.4 | 0.9 | 96.3 | 14.9 |
| A549 | 16R548_0005_A549024T | | 447.0 | 280 | 70 | | | 7809826 | 86.9 | 48.2 | 114.2 | 0.8 | 95.6 | 18.2 |
| A549 | 16R549_0006_A549048T | | 199.8 | 272 | 70 | | | 9277450 | 86.5 | 47.3 | 98.6 | 1 | 96.8 | 28 |
| A549 | 16R552_0009_A549S06T | S1, protocol B | 762.0 | 264 | 70 | | | 7402026 | 86.7 | 48.7 | 124.5 | 1.1 | 90.4 | 10 |
| A549 | 16R553_0010_A549S12T | | 720.0 | 264 | 70 | | | 7408662 | 86.7 | 51.3 | 130.8 | 1 | 92 | 11.1 |
| A549 | 16R554_0011_A549S24T | | 576.0 | 259 | 70 | | | 7596838 | 85.8 | 48 | 123.1 | 1 | 91.7 | 11.6 |
| A549 | 16R555_0012_A549S48T | | 432.0 | 264 | 70 | | | 9427018 | 86.2 | 49.5 | 156.3 | 0.9 | 96.1 | 14.4 |

Indeed, in order to confirm whether the nick of the FFPE tissue DNA occurs in the formaldehyde fixation process, 1. FFPE cell tissue was prepared using the cultured cells (A549), 2. Fixation time of formaldehyde was varied to 3/6/12/24/48 hours, and then embedded in paraffin to prepare a cell block, 3. Each DNA library was prepared by Covaris and S1 nuclease treatment methods, and the amount and size of the prepared library were measured, 4. NGS sequencing was performed to compare the quality of the produced data.

As a result, the longer the formaldehyde fixation time was, the smaller the size of fragmented DNA during S1 nuclease treatment was. This means that the longer the formaldehyde fixing time is, the more nicks which are active sites of S1 nucleases are generated (FIG. 12).

In addition, four cell block DNAs extracted by the Covaris method and the S1 nuclease treatment method were subject to library preparation, captured simultaneously using the AMCv2 panel in the same amount, subjected to NGS sequencing and the results were compared (Table 10).

The above results are summarized as follows.

1. The longer the formaldehyde fixation time is, the smaller the size of the fragmented DNA during S1 enzyme treatment is.

2. In the case of the Covaris method, as the fixation time increased, the quantity and quality of the prepared library became significantly worse, thereby reducing the amount of sequencing data.

3. In the S1 nuclease method, as the fixation time increased, the amount of prepared library was rather increased, there was no significant difference in quality and there was no significant difference in the amount of sequencing data.

The invention claimed is:

1. A method of preparing a DNA library derived from formalin-fixed paraffin-embedded (FFPE) tissue having improved complexity comprising:
   fragmenting DNA by applying only an endonuclease that cleaves at nicks in dsDNA derived from the FFPE tissue, wherein the DNA is eluted from the FFPE tissue during the fragmenting step.

2. The method of preparing a DNA library derived from FFPE tissue having improved complexity of claim 1, wherein the endonuclease is applied to a FFPE tissue slice lysate obtained by decomposing and removing a protein from a FFPE tissue slice of the FFPE tissue.

3. The method of preparing a DNA library derived from FFPE tissue having improved complexity of claim 1, wherein the step of fragmenting further comprises subjecting to end-repair of both ends of the DNA and ligating the end-repaired DNA.

4. The method of preparing a DNA library derived from FFPE tissue having improved complexity of claim 2, wherein the endonuclease with 1 to 100 units is applied to the FFPE tissue slice lysate.

5. The method of preparing a DNA library derived from FFPE tissue having improved complexity of claim 1, wherein the endonuclease is applied at 37° C. for 1 to 60 minutes.

6. The method of preparing a DNA library derived from FFPE tissue having improved complexity of claim 1, the endonuclease is at least any one selected from the group consisting of S1 nuclease, P1 nuclease, mung bean nuclease and BAL-31 nuclease.

7. The method of preparing a DNA library derived from FFPE tissue having improved complexity of claim 1, wherein the DNA library is for NGS analysis.

8. A method of eluting a DNA fragment derived from formalin-fixed paraffin-embedded (FFPE) tissue, comprising:

fragmenting DNA by applying only an endonuclease at nicks in dsDNA derived from FFPE tissue, wherein the DNA is eluted from the FFPE tissue during the fragmenting step.

9. The method of eluting a DNA fragment derived from FFPE tissue of claim 8, wherein the endonuclease is applied to a FFPE tissue slice lysate obtained by decomposing and removing a protein from a FFPE tissue slice of the FFPE tissue.

10. The method of eluting a DNA fragment derived from FFPE tissue of claim 9, wherein the endonuclease with 1 to 100 units is applied to the FFPE tissue slice lysate.

11. The method of eluting a DNA fragment derived from FFPE tissue of claim 8, wherein the endonuclease is applied at 37° C. for 1 to 60 minutes.

12. The method of eluting a DNA fragment derived from FFPE tissue of claim 8, the endonuclease is at least any one selected from the group consisting of S1 nuclease, P1 nuclease, mung bean nuclease and BAL-31 nuclease.

* * * * *